(12) United States Patent  
Phillips et al.

(10) Patent No.: US 11,910,831 B2  
(45) Date of Patent: Feb. 27, 2024

(54) VAPORIZER HEATING ELEMENT ASSEMBLIES AND METHODS OF MANUFACTURING SAME

(71) Applicant: Blackship Technologies Development LLC, North Chesterfield, VA (US)

(72) Inventors: Donovan Phillips, North Chesterfield, VA (US); Yongjie Xu, North Chesterfield, VA (US)

(73) Assignee: Blackship Technologies Development LLC, North Chesterfield, VA (US)

( * ) Notice: Subject to any disclaimer, the term of this patent is extended or adjusted under 35 U.S.C. 154(b) by 591 days.

(21) Appl. No.: 17/117,510

(22) Filed: Dec. 10, 2020

(65) Prior Publication Data

US 2022/0183362 A1 Jun. 16, 2022

(51) Int. Cl.
| | |
|---|---|
| *A24F 40/46* | (2020.01) |
| *A24F 40/70* | (2020.01) |
| *A24F 40/10* | (2020.01) |
| *A24F 40/42* | (2020.01) |
| *A24F 40/44* | (2020.01) |

(Continued)

(52) U.S. Cl.
CPC ............. *A24F 40/46* (2020.01); *A24F 40/10* (2020.01); *A24F 40/42* (2020.01); *A24F 40/44* (2020.01); *A24F 40/48* (2020.01); *A24F 40/70* (2020.01); *B29C 45/0053* (2013.01); *B29C 45/14639* (2013.01); *B29C 65/08* (2013.01); *H05B 3/22* (2013.01); *A61M 15/06* (2013.01); *B29L 2031/7414* (2013.01); *B29L 2031/753* (2013.01)

(58) Field of Classification Search  
CPC .......... A24F 40/46; A24F 40/10; A24F 40/70; A24F 40/48  
See application file for complete search history.

(56) References Cited

U.S. PATENT DOCUMENTS

| | | | |
|---|---|---|---|
| 10,172,388 | B2 | 1/2019 | Sears et al. |
| 10,517,331 | B2 | 12/2019 | Atkins et al. |

(Continued)

FOREIGN PATENT DOCUMENTS

WO 2020223876 A1 11/2020

OTHER PUBLICATIONS

International Searching Authority, International Search Report and Written Opinion, International Application No. PCT/US21/62539, dated Feb. 25, 2022, pp. 1-13.

*Primary Examiner* — Hae Moon Hyeon  
(74) *Attorney, Agent, or Firm* — Nixon & Vanderhye P.C.

(57) ABSTRACT

A vaporizer heating element assembly has a case structure with a plurality of walls collectively defining a case interior. An upper wall has an access opening, a left wall has a reservoir window, and a lower wall has a vaporization window. A thin plate heating element formed from an electrically conductive material is positioned within the case structure parallel to the lower wall and adjacent the vaporization window. A liquid transport structure is configured for transporting liquid by capillary action from a liquid intake surface to a liquid outflow surface and is disposed within the case interior so that the liquid intake surface is adjacent the reservoir window and the liquid outflow surface is adjacent or in contact with the thin plate heating element. The heating element assembly also has an access closure sized and configured to seal the access opening.

21 Claims, 13 Drawing Sheets

(51) Int. Cl.
*B29C 45/14* (2006.01)
*B29C 45/00* (2006.01)
*A24F 40/48* (2020.01)
*H05B 3/22* (2006.01)
*B29C 65/08* (2006.01)
*A61M 15/06* (2006.01)
*B29L 31/00* (2006.01)

(56) References Cited

U.S. PATENT DOCUMENTS

| | | | |
|---|---|---|---|
| 11,457,663 B2 * | 10/2022 | Xie | A24F 40/44 |
| 2011/0155153 A1 * | 6/2011 | Thorens | H05B 3/58 |
| | | | 131/329 |
| 2016/0309785 A1 * | 10/2016 | Holtz | H05B 3/141 |
| 2016/0345631 A1 | 12/2016 | Monsees et al. | |
| 2018/0263290 A1 | 9/2018 | Collett et al. | |
| 2019/0001077 A1 | 1/2019 | Xu et al. | |
| 2020/0113246 A1 | 4/2020 | Barbaric et al. | |
| 2020/0154779 A1 | 5/2020 | Novak, III et al. | |
| 2020/0164162 A1 | 5/2020 | Phillips et al. | |
| 2020/0260785 A1 | 8/2020 | Bowen et al. | |
| 2022/0125108 A1 * | 4/2022 | Zhou | A24F 40/44 |
| 2022/0183355 A1 * | 6/2022 | Phillips | A24F 40/44 |
| 2022/0183361 A1 * | 6/2022 | Phillips | H05B 3/24 |

* cited by examiner

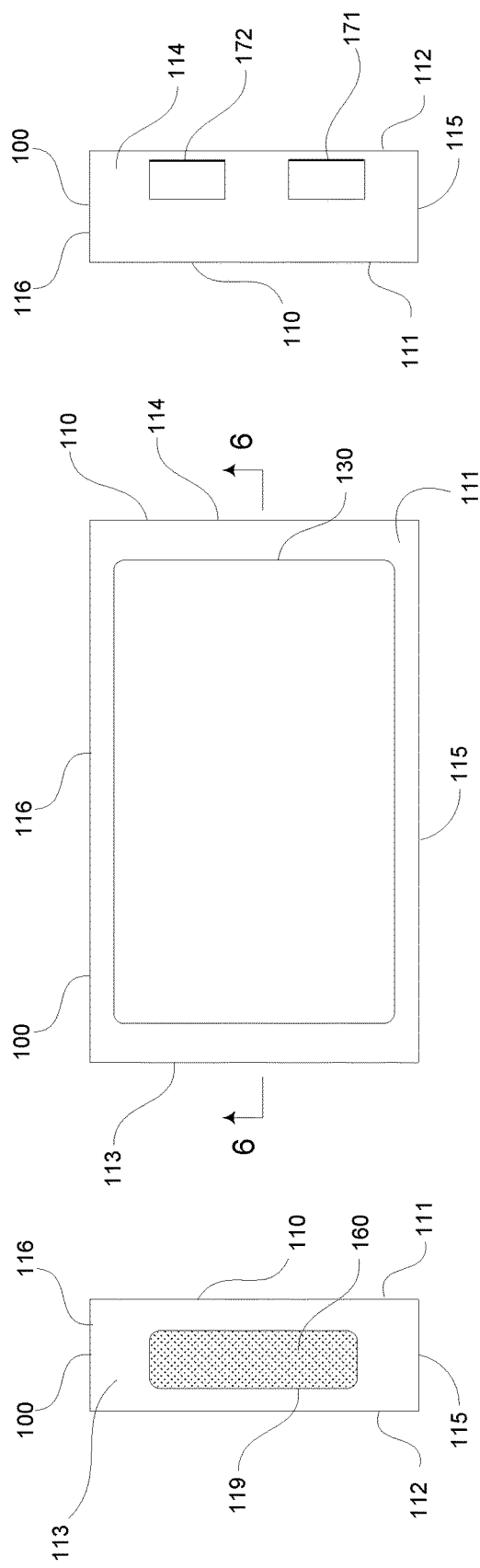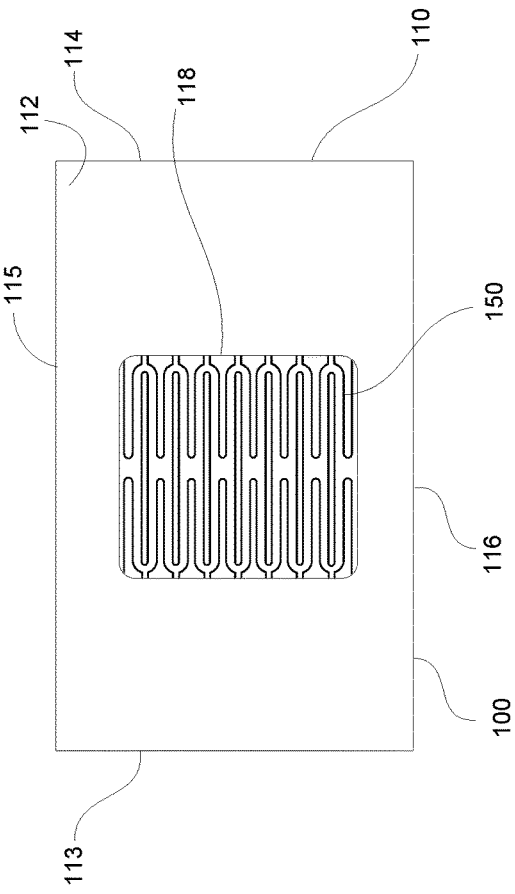

VAPORIZER HEATING ELEMENT ASSEMBLIES AND METHODS OF MANUFACTURING SAME

BACKGROUND OF THE INVENTION

The present invention relates generally to micro-vaporizer heaters and, more particularly, to modular heating element assemblies that can be used in multiple vaporizer configurations and to methods of manufacturing such modular assemblies.

Liquid vaporizing devices (referred to herein as vaporizers or micro-vaporizers) are devices in which a vaporizable liquid is drawn from a storage reservoir into a chamber where it is heated to vaporization temperature by a heating element. The vaporized liquid is then drawn or forced from the chamber. In products such as electronic cigarettes (also known as e-cigarettes or personal vaporizers), the vaporized liquid is drawn from the chamber through a mouthpiece and inhaled by the user. In other products the vaporized liquid is dispersed into the atmosphere.

Conventional micro-vaporizers use a wick to draw vaporizable liquid from a reservoir into the vaporization chamber where it is brought into close proximity with the heating element. The heating element itself typically includes a coiled heating wire that may be positioned near a surface of the wick or, in some cases, may be wrapped around a portion of the wick. Coiled wire heaters have a number of drawbacks relating to efficiency and cost to manufacture and may require that the wick material and configuration be tailored to the heater. With the growing popularity of low cost, throwaway personal vaporization devices, a high efficiency, lower cost alternative to the conventional wick/heating element approach is needed.

SUMMARY OF THE INVENTION

An illustrative aspect of the invention provides a vaporizer heating element assembly comprising a case structure having a plurality of walls collectively defining a case interior. The plurality of walls include an upper wall having an access opening formed there-through, a left wall having a reservoir window formed there-through, and a lower wall having a vaporization window formed there-through. The assembly further comprises a thin plate heating element formed from an electrically conductive material. The thin plate heating element is positioned in the case structure parallel to the lower wall and adjacent the vaporization window. The assembly also comprises a liquid transport structure having a liquid intake surface and a liquid outflow surface. The liquid transport structure is configured for transporting a vaporizable liquid by capillary action from the liquid intake surface to the liquid outflow surface. The structure is disposed within the case interior so that the liquid intake surface is adjacent the reservoir window and the liquid outflow surface is adjacent or in contact with a surface of the thin plate heating element. The heating element assembly also comprises an access closure disposed within the access opening and attached to the upper wall, the access closure being sized and configured to seal the access opening.

Another illustrative aspect of the invention provides a method of manufacturing a vaporizer heating element assembly. The method comprises providing a thin plate heating element formed from an electrically conductive material and positioning the thin plate heating element within an injection mold. The injection mold is configured for receiving molten plastic material and forming it into a case structure having a plurality of walls collectively defining a case interior. The plurality of walls include an upper wall having an access opening formed there-through, a left wall having a reservoir window formed there-through, and a lower wall having a vaporization window formed there-through. The method further comprises injecting molten plastic into the injection mold to produce a molded plastic case structure in which the thin plate heating element is positioned in the case interior parallel to the lower wall adjacent the vaporization window. A portion of the thin plate heating element is embedded within one or more of the plurality of walls. After injection, the molded plastic case structure and the thin plate heating element are removed from the injection mold. The method still further comprises providing a liquid transport structure having a liquid intake surface and a liquid outflow surface. The liquid transport structure is configured for transporting liquid by capillary action from the liquid intake surface to the liquid outflow surface. The liquid transport structure is then inserted into the case interior through the access opening and positioned it so that the liquid intake surface is adjacent the reservoir window and the liquid outflow surface is adjacent or in contact with a surface of the thin plate heating element. The method also comprises sealing the access opening with a closure element sized and configured to be partially received into the access opening.

Another illustrative aspect of the invention provides a vaporizer comprising a vaporizer housing having a housing interior and an exterior and a reservoir disposed within the housing interior. The reservoir has a reservoir exit port and is configured for selectively retaining a vaporizable liquid therein. The vaporizer further comprises an air inlet passage in fluid communication with the exterior via an inlet port, a vaporization chamber within the housing interior in fluid communication with the air inlet passage, and a vaporization products passage in fluid communication with the vaporization chamber and with the exterior via a vaporization product outlet. The vaporizer still further comprises electrical circuitry comprising a power source, a control processor, and positive and negative heating element contacts. The control processor is configured for controlling application of power from the power source to the heating element contacts. The vaporizer also comprises a heating element receiving well formed within the housing interior and a heating element assembly operably disposed within the receiving well. The heating element assembly comprises a case structure defining a case interior, a thin plate heating element formed from an electrically conductive material, and a liquid transport structure. The case structure has a reservoir window and a vaporization window formed there-through. The case structure and receiving well are collectively configured so that when the heating element assembly is received into the receiving well, the reservoir window is in registration with the reservoir exit port and the vaporization window is adjacent the vaporization chamber. The thin plate heating element is positioned within the case interior so that at least a portion of the heating element is adjacent the vaporization window. The liquid transport structure is disposed within the housing interior so that the liquid intake surface is adjacent the reservoir window and the liquid outflow surface is adjacent or in contact with a surface of the thin plate heating element.

BRIEF DESCRIPTION OF THE DRAWINGS

The invention can be more fully understood by reading the following detailed description together with the accompanying drawing, in which like reference indicators are used to designate like elements, and in which:

FIGS. 2A, 2B, 2C, and 2D are left, top, right and bottom views respectively of a heating element assembly according to an embodiment of the invention;

DETAILED DESCRIPTION OF THE INVENTION

Typical micro-vaporizers have a reservoir from which vaporizable liquid is drawn (typically through the use of a wick) to a vaporization chamber. There the liquid is brought into close proximity with a heating element. The heating element and, generally, a portion of the wick are disposed within the vaporization chamber. When the heating element is activated, the liquid from the wick is vaporized/aerosolized. The resulting vaporization products and unvaporized liquid are mixed with air that is drawn from outside the device into the vaporization chamber. The mixture is then released from or drawn out of the device.

Figure 1:
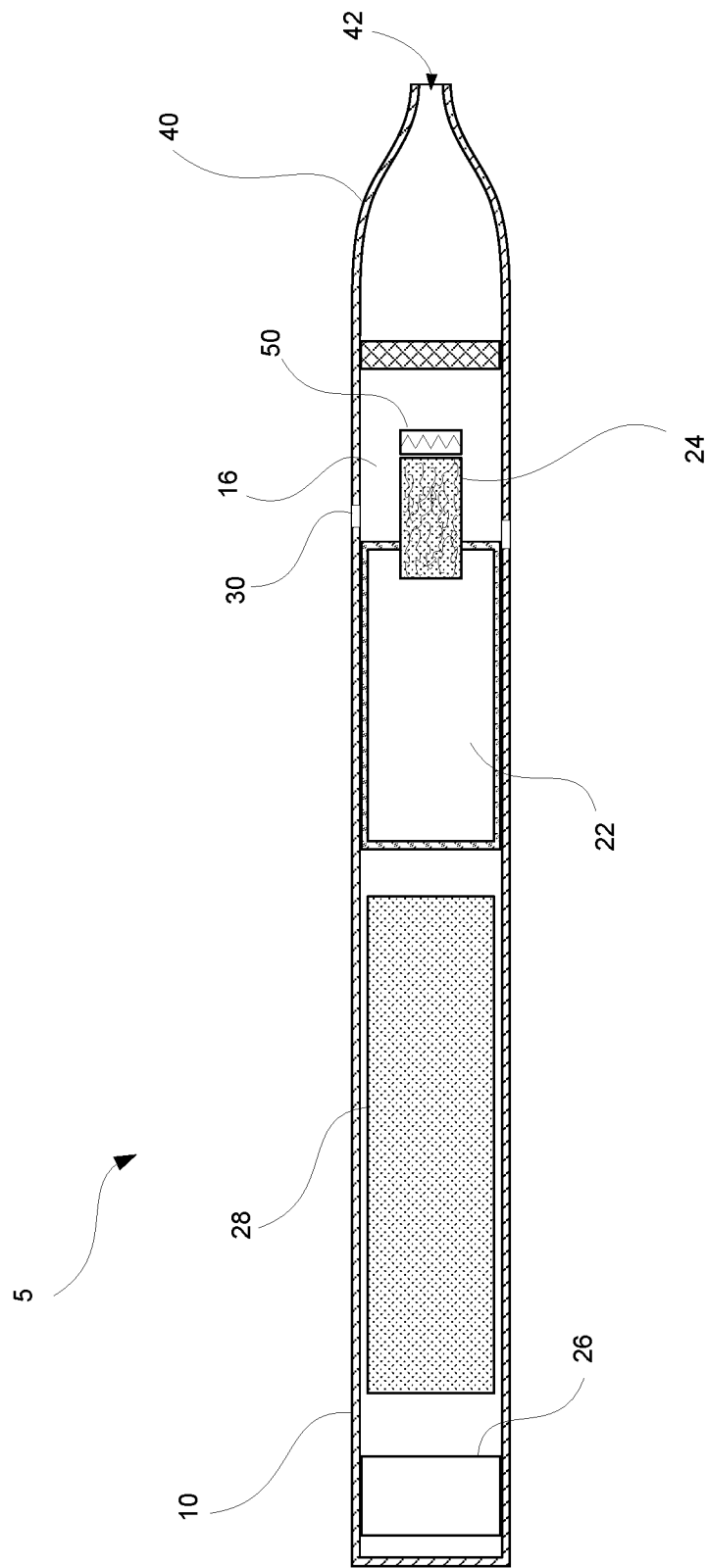
FIG. 1 is a section view of a prior art personal vaporizer.
Figure 3:
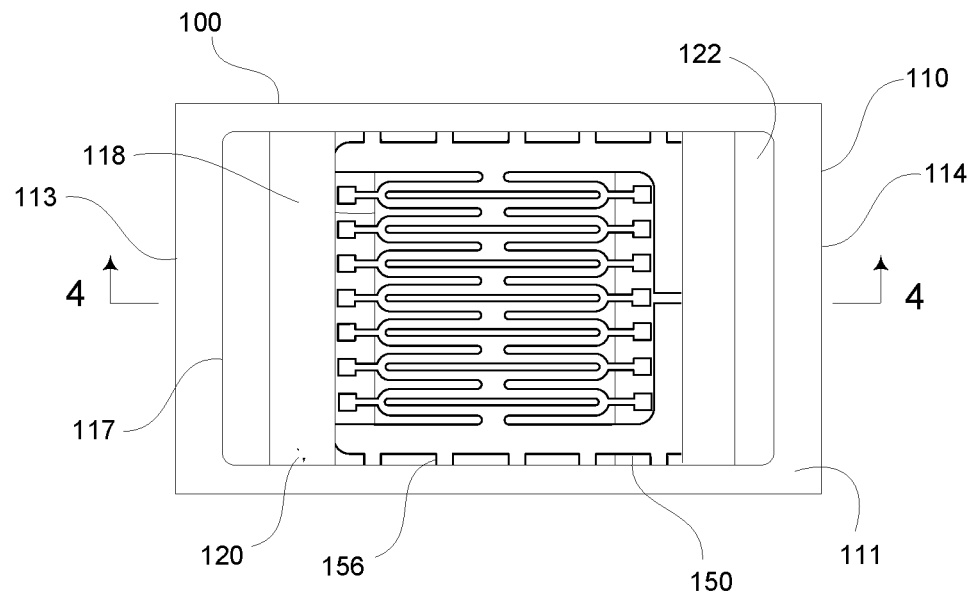
FIG. 3 is a top view of the case structure and thin plate heating element of the heating element assembly of FIG. 2.

As shown in FIG. 1, a typical prior art personal vaporizer 5 has an outer case (or housing) 10 with an air intake passage (or passages) 30 that provide air to a vaporization chamber 16. The personal vaporizer 5 has a liquid reservoir 22 in which is disposed a vaporizable liquid. A liquid transport structure 24 (e.g., a wick) is configured and positioned to be in contact with the liquid in the reservoir 22 and for drawing the liquid out of the reservoir 22 and into the vaporization chamber 16 in close proximity or in contact with a heating element (or heater) 50. The illustrative personal vaporizer 5 also comprises a battery 28 for powering the heating element 50 and a control unit 26. When the heater 50 is activated, liquid from the liquid transport structure is heated and vaporized and mixed with air in the vaporization chamber 16. The resulting mixture is drawn through into and through a mouthpiece 40 and out through the exit 42 where it is inhaled by the user.

The heating element 50 may be configured to heat the vaporizable liquid through any conductive, convective, and/or radiative heat transfer mechanism. In typical vaporizers, the heating element 150 is or includes a resistance element in the form of a wire coil. As previously noted, coiled wire heating elements have significant drawbacks. While plate-like heating elements have been used in vaporizer devices, they have suffered from many of the same drawbacks as coiled wire heaters. This is due, at least in part, to the requirement for an expensive base material and/or multiple materials and substrates. These aspects may make the resulting heater as expensive as or more expensive than a comparable coiled wire heater. The prior art heaters may also be difficult or impossible to use in conjunction with certain vaporizer housing materials due to heat conduction issues.

The present invention provides a heating element assembly in the form of a module having a molded plastic case and internal structure in which an electrically conductive, thin plate heating element is embedded and in which a liquid transport structure is disposed adjacent or in contact with the heating element. The assembly may be structured so that the plastic structure is molded around the heating element to permanently hold it in place without the need for gaskets, seals, or thermal isolation. Any of a variety of liquid transport structures may then be selected and positioned within the structure which can then be sealed to provide a self-contained module. The module can then be used to provide the heating and liquid transport functions for any of a variety of vaporizers configured to receive the heating element module.

FIGS. 2-6 illustrate a heating element assembly 100 according to an illustrative embodiment of the invention. The heating element assembly 100 has a generally rectangular prism-shaped case structure 110 with a heating element 150 partially embedded in a portion of the case structure 110. The case structure 110 has an interior space 120 in which may be disposed a liquid transport structure 160. In addition, the heating element 150 may be in the form of a thin wall heating element and/or a thin plate heating element.

The case structure 110 has upper and lower case walls 111, 112, a left (or reservoir) side case wall 113, a right (or contact) side case wall 114, and front and back case walls 115, 116 that collectively define the case interior space 120. The lower wall 112 has a vaporization product flow window 118 formed there-through. The heating element 150 is partially embedded in the lower wall 112 in such a way that it spans the vaporization product flow window 118. As will be discussed in more detail below, the heating element 150 may be configured so that the portion of the heating element 150 framed by the vaporization product flow window 118 is configured for heating vaporizable liquid from the liquid transport structure 160 and for allowing passage of liquid and vaporization products through the heating element 150 and out of the heating element assembly 100.

Figure 4:
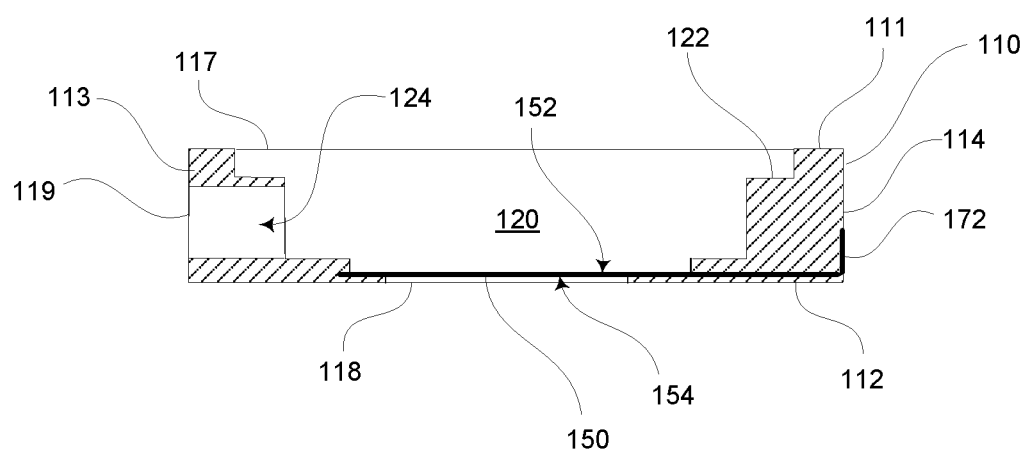
FIG. 4 is a front section view of the case structure and thin plate heating element of the heating element assembly of FIG. 2.
Figure 6:
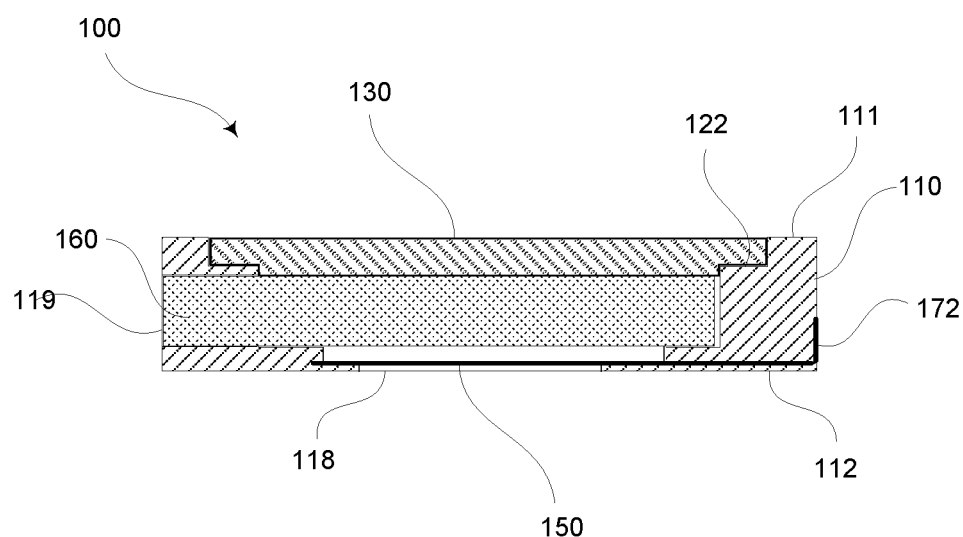
FIG. 6 is a front section view of the heating element assembly of FIG. 2.

As best seen in FIG. 4, the upper case wall 111 has an access opening 117 formed there-through. The access opening 117 is sized and configured to allow access to the interior space 120 during the construction of the heating element assembly 100. As best seen in FIGS. 2B and 6, a top wall closure member 130 may be received into the access opening 117 to rest on a closure support ledge 122 in the interior space 120, thereby closing off the access opening 117.

The components of the case structure 110 and the closure member 130 may be formed from heat-resistant thermoplastic materials including, but not limited to copolyesters such as Eastman Tritan. While the case structure walls 111-116 may be constructed individually and bonded to one another, they are preferably formed as a single integral structure. In particular embodiments, the case structure 110 is formed by injection molding of a suitable plastic material such as the aforementioned Tritan. The size and thickness of the walls may be determined by the application. Typical minimum wall thicknesses may be in a range of 0.01 mm to 1.00 mm.

The reservoir side case wall 113 has a reservoir communication window 119 formed there-through. The reservoir communication window 119 is sized and configured to provide fluid communication between a vaporizer device reservoir (or a flow structure leading from such a reservoir) and the interior space 120 when the heating element assembly 100 is installed in the vaporizer device. The reservoir side case wall 113 may further define a channel 124 leading from the window 119 into the interior space 120. The channel 124 may be sized to receive a portion of the liquid transport structure 160 so that an intake surface 162 of the liquid transport structure 160 may be positioned at or adjacent the window 119. In this way, the liquid transport structure 160 may be placed in communication with liquid in the vaporizer reservoir by positioning the heating element assembly 100 within a vaporizer so that the reservoir communication window 119 is in registration with a passage into the vaporizer's reservoir. In some embodiments, the liquid transport structure 160 may be sized to extend through the window 119 so that when the heating element assembly 100 is installed, the liquid transport structure extends into the vaporizer reservoir or a passage in communication therewith.

The liquid transport structure 160 is configured for drawing vaporizable liquid from a reservoir through the upstream intake surface 162 into the liquid transport structure 160 and transporting the liquid to a downstream outflow surface 164 where the liquid may be heated to vaporization by the heating element 150. The liquid transport structure 160 may be or comprise a wick or collection of wicking material. Typical personal vaporizer wicks are formed from organic fiber materials such as cotton, jute, flax, cellulose, or hemp. Some inorganic materials such as silica, carbon, and non-organic polymer fibers, ceramics and steel mesh may also be used. In general, vaporizer wicks can be formed from any material that is thermally stable and that provides sufficient wicking action to transport the vaporizable liquid from the reservoir to the heating element 150. The liquid transport structure 160 may also comprise a composite wick formed from a combination of wicking materials and active materials. The liquid transport structure may, in particular be or include any of the composite wicks disclosed in U.S. patent application Ser. No. 15/639,139, filed Jun. 30, 2017 (the "'139 Application"), the complete disclosure of which is incorporated herein by reference in its entirety. Composite wick materials may include woven or non-woven fibrous wicking materials in combination with embedded, trapped, adhered or alternately layered active additive materials. They are generally configured so that, in transport from the liquid reservoir, the vaporizable liquid must come into contact with the active additive materials. Portions of the active additive materials may be released into the fluid or may otherwise affect or impart desired characteristics to the liquid.

While the liquid transport structure 160 in the illustrated embodiment is a configured as a rectangular block, it will be understood that other shapes may be used including cylinders, flat sheets or bent elongate elements. It will also be understood that the interior space 120 may be shaped to receive and retain various shaped liquid transport structures 160.

The heating element 150 may be configured for placement in contact with or adjacent the downstream outflow surface 164 of the liquid transport structure 160. While any flat plate heating element may be usable in embodiments of the invention, in preferred embodiments, the heating element 150 has a central portion configured for heating vaporizable liquid in the liquid transport structure 160 at or adjacent the outflow surface 164 and a peripheral portion that supports the central heating portion and to connect the central heating portion to a power source. Flat plate heating elements with such attributes are disclosed in U.S. application Ser. No. 17/117,373, filed Dec. 10, 2020, the complete disclosure of which is incorporated herein by reference. The heating element 150 may be configured so that the only contact between the heating element 150 and the case structure 110 is through the peripheral portion of the heating element. This isolation of the central heating portion allows the use of case materials that would otherwise be unable to withstand the heat generated by the heating element 150.

Figure 7:
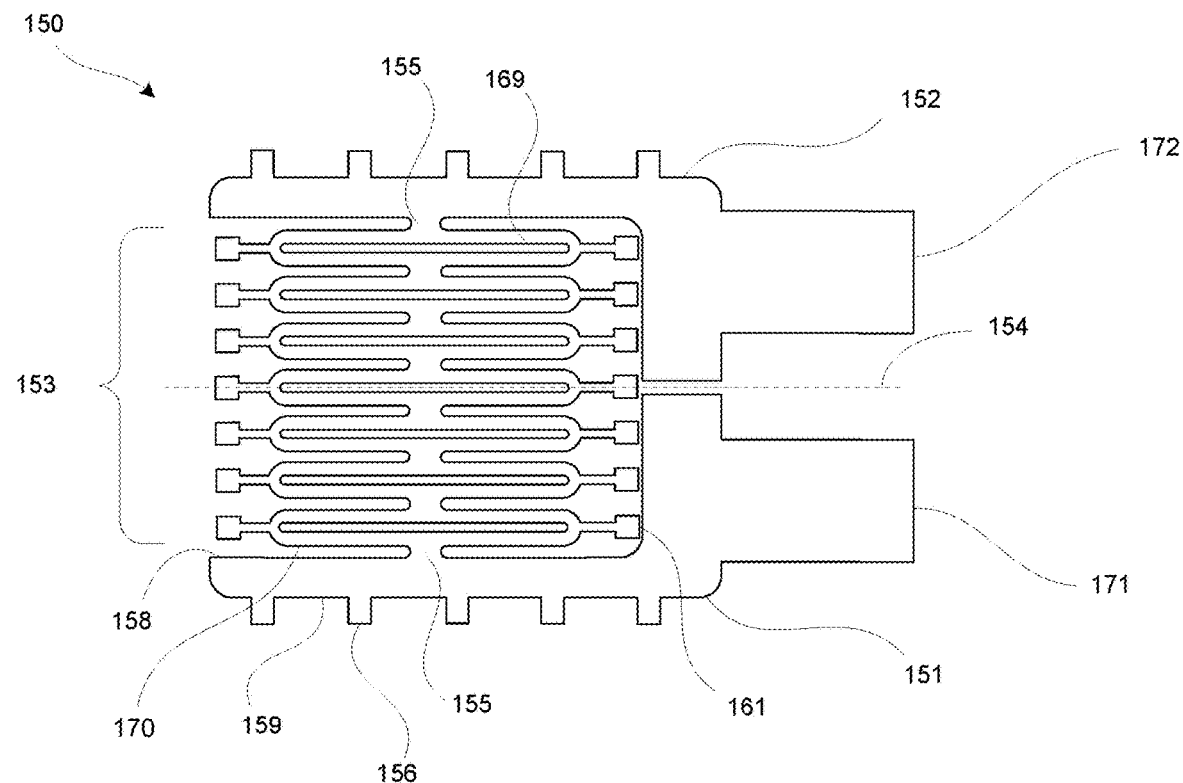
FIG. 7 is a plan view of a thin plate heating element usable in embodiments of the invention.

FIG. 7 illustrates an exemplary thin plate heating element 150 usable in embodiments of the invention. The heating element 150 is formed from a single planar sheet of electrically conductive material having a constant sheet thickness. The material and thickness used may be selected to provide a desired combination of electrical and thermal properties as well as a desired degree of structural integrity and/or rigidity. Illustrative materials that could be used include carbon, graphite, metals, metal alloys, electrically conductive ceramics (such as, for example, molybdenum disilicide), and composite materials made of a ceramic material and a metallic material. Composite materials may include doped ceramics such as doped silicon carbides. Suitable metals may include titanium, zirconium, tantalum and metals from the platinum group. Suitable metal alloys may include nichrome, kanthal, stainless steel, constantan, nickel-, cobalt-, chromium-, aluminum-, titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminum based alloys and ironmanganese-aluminum based alloys. Typical sheet thicknesses for such materials may be in a range of 0.00005 in. to 0.15000 in.

Figure 8:
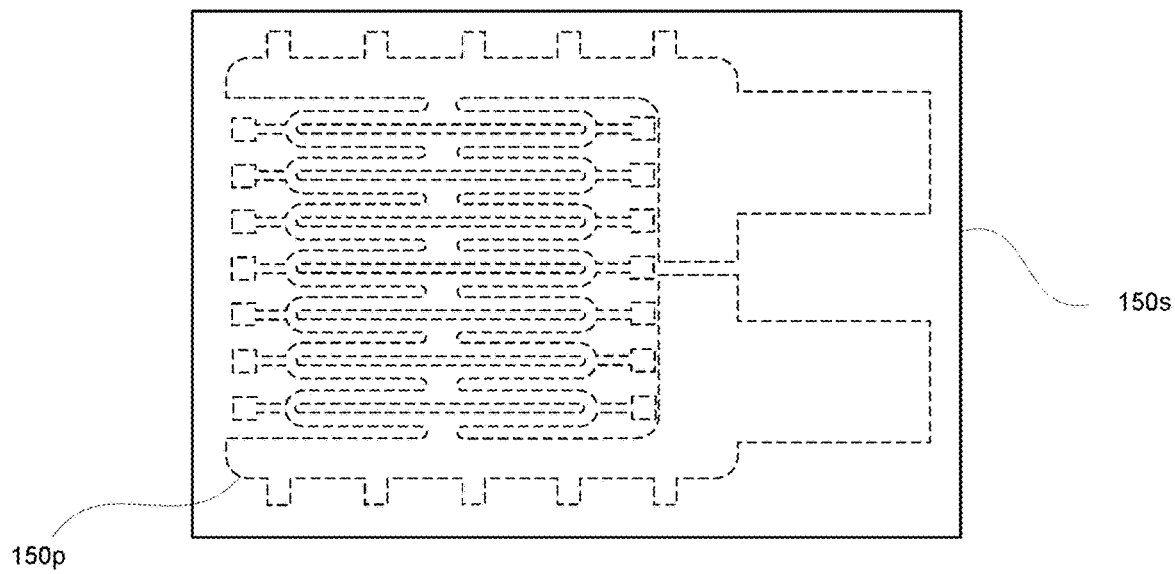
FIG. 8 is a plan view of a thin plate heating element blank.

Thin plate heating elements usable in the present invention may be manufactured from a single thin sheet of conductive material. With reference to FIG. 8, the heating element 150, for example, may be cut from a planar sheet of material 150s according to a pattern 150p. Features of the heating element may be formed by cutting a pattern of channels through the material to provide a flow path for vaporizable liquid and vaporization products to flow through. This may be accomplished, for example, using any suitable cutting tool (e.g., a laser or water jet) or by punching or chemical etching.

The resulting heating element 150 has a peripheral conduction portion made up of a positive support arm 151 and a negative support arm 152 and a central heating portion 153 positioned between the support arms 151, 152. The support arms 151, 152 have interior edges 158 facing inward toward one another and toward the central heating portion 153 and exterior lateral edges 159 facing outward. The interior edges 158 are parallel to one another and to a longitudinal axis 154. The positive support arm 151 includes a positive contact tab 171 and the negative support arm 152 includes a negative contact tab 172 extending in a longitudinal direction away from the central heating portion 153. The positive and negative contact tabs 171, 172 are configured for making electrical contact with corresponding elements of an electrical power circuit in communication with a power source.

In particular embodiments, the heating element 150 may have a plurality of peripheral support tabs 156 extending laterally outward from the exterior edges 159 of the support arms 151, 152. These support tabs 156 may be sized and configured to engage surfaces or to be engaged by other structures in order to support and/or hold the heating element 150 in place within the case structure 110.

Figure 9:
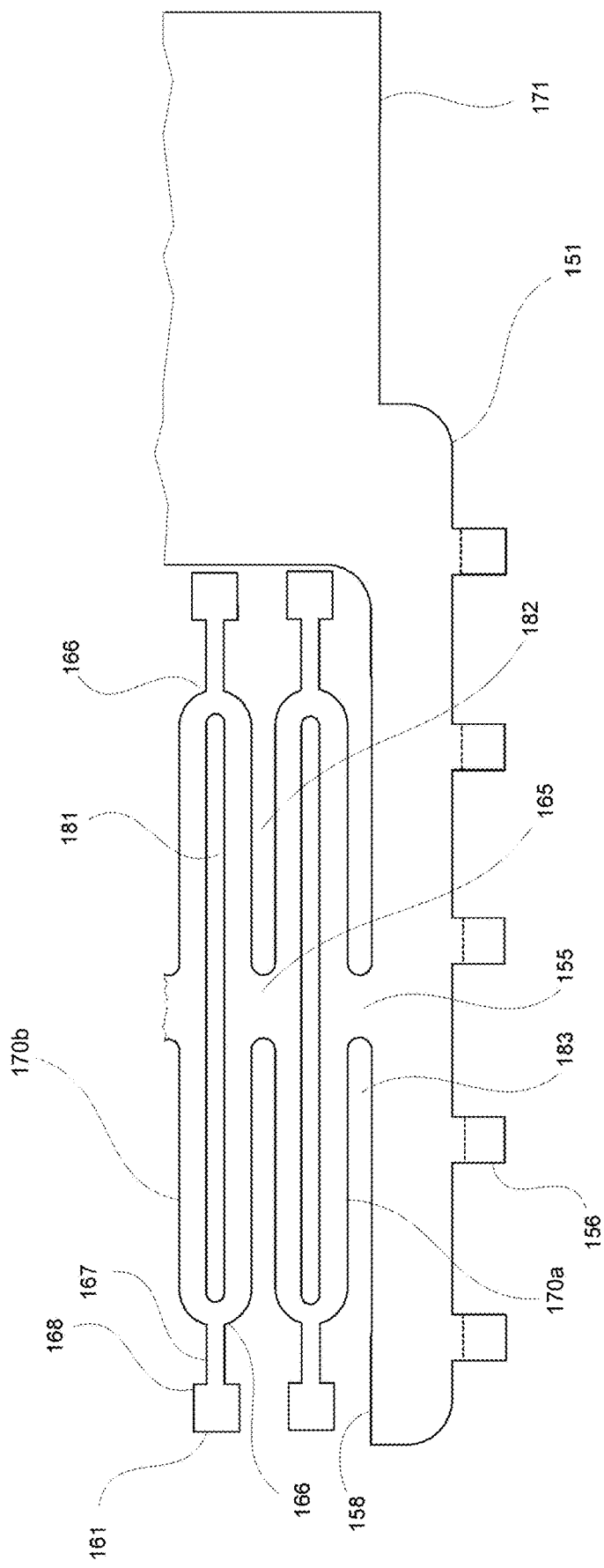
FIG. 9 is an enlarged view of a portion of the thin plate heating element of FIG. 7.
Figure 10:
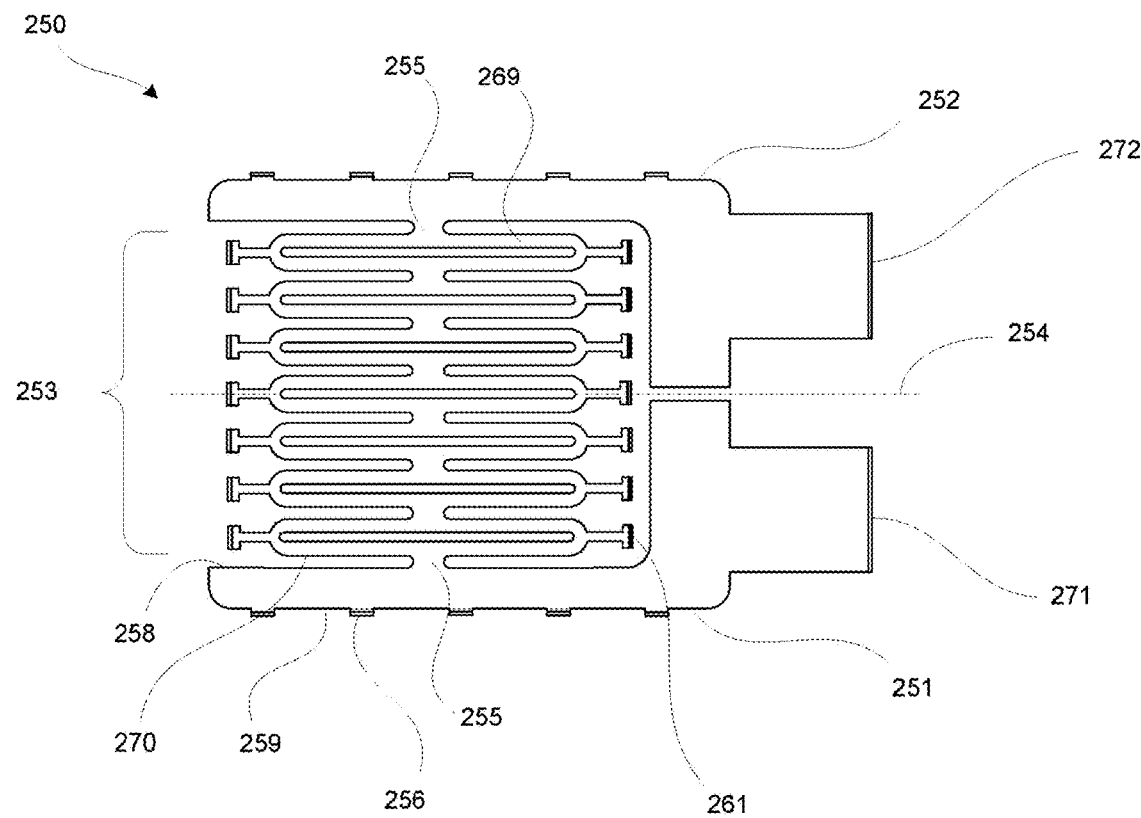
FIG. 10 is a plan view of a thin plate heating element usable in embodiments of the invention.
Figure 11:
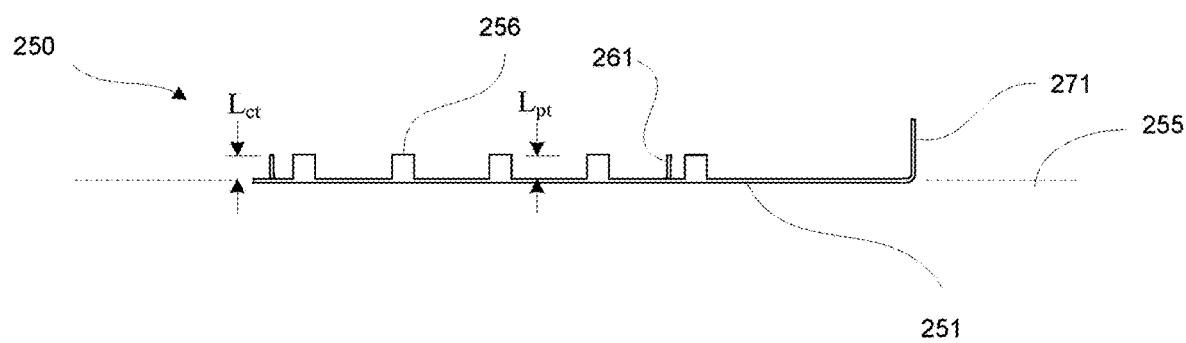
FIG. 11 is a side view of the thin plate heating element of FIG. 10.
Figure 12:
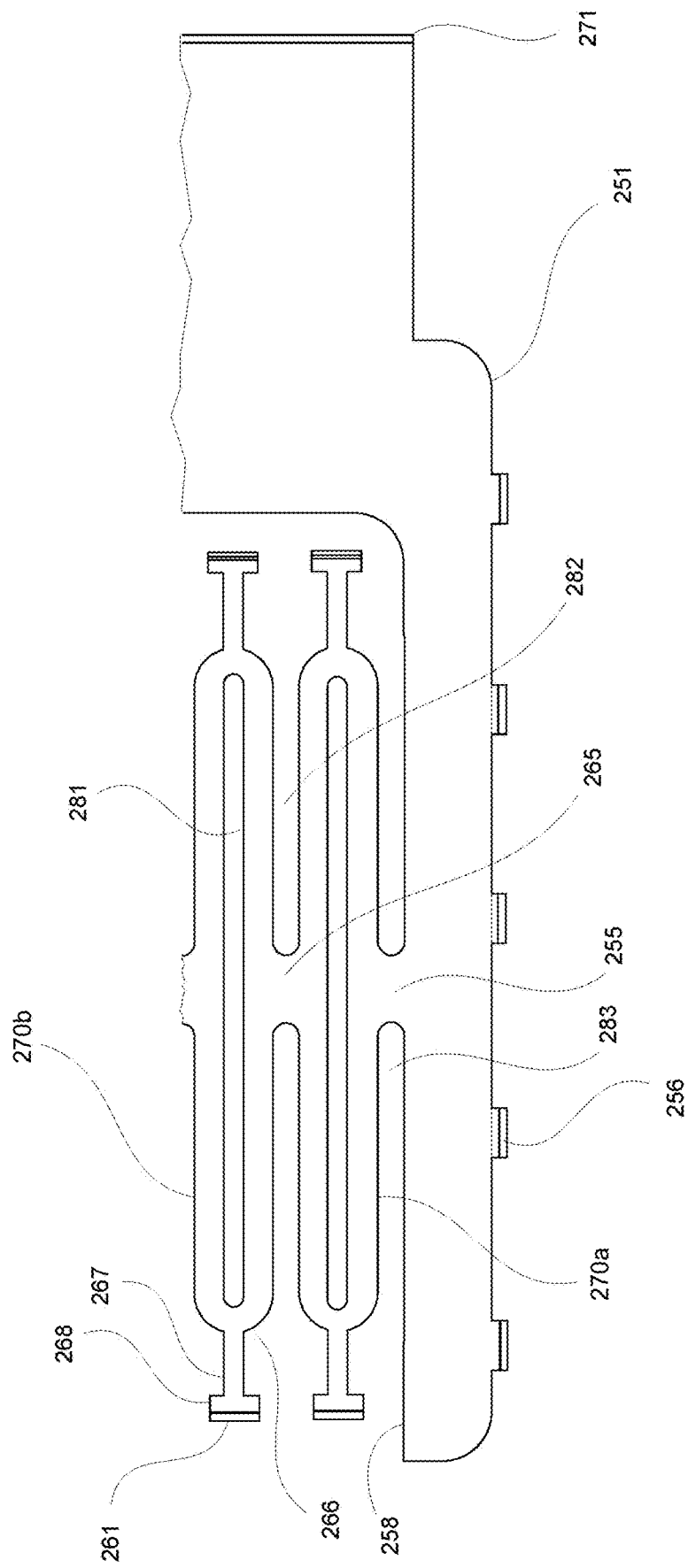
FIG. 12 is an enlarged view of a portion of the thin plate heating element of FIG. 10.
Figure 13:
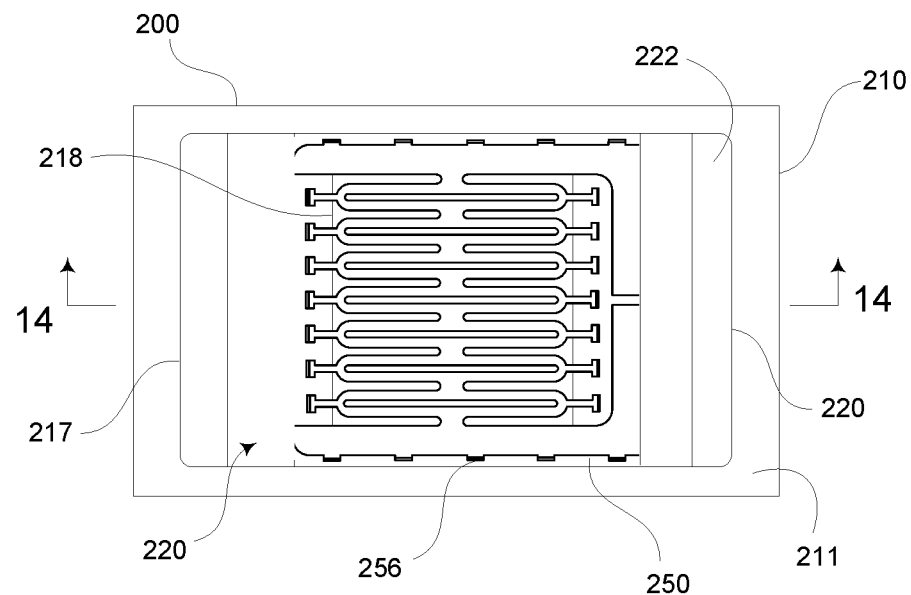
FIG. 13 is a top view of the case structure and thin plate heating element of a heating element assembly according to an embodiment of the invention.
Figure 14:
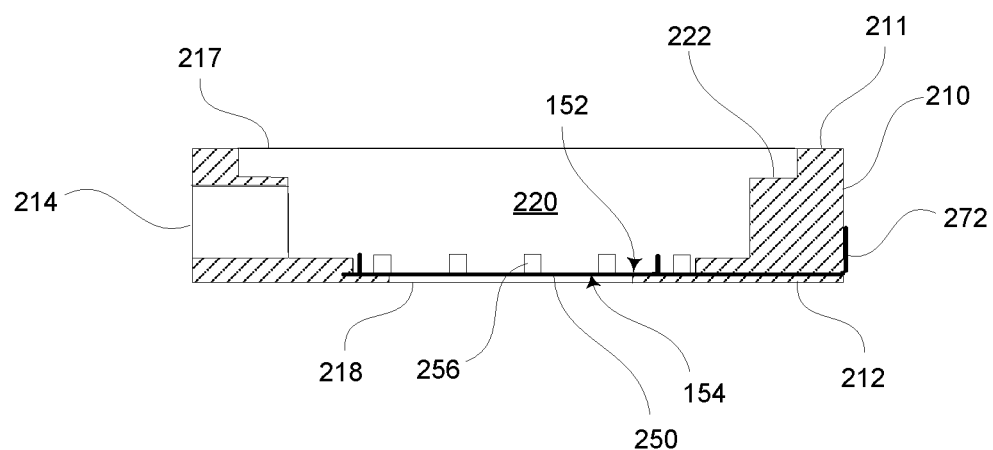
FIG. 14 is a front section view of the case structure and thin plate heating element of FIG. 13.

With reference to FIGS. 7 and 9, the central heating portion 153 is made up of an array of spaced apart but interconnected heating strips 169. These heating strips 169 are parallel to one another and to the longitudinal axis 154. In particular embodiments and as illustrated in FIG. 7, the heating strips 169 are divided in to pairs, with the heating strips 169 of each pair being connected to one another at both ends to form a heating element loop 170 surrounding a through channel 181 through the material. In the illustrated embodiment, the loop ends 166 are arcuate, but it will be understood that in other embodiments, the end connections could be straight, thereby forming a "squared off" loop. Adjacent heating element loops 170 (e.g., loop 170a and loop 170b) are connected to one another by a lateral strip 165. Adjacent heating strips 169 of adjacent heating element loops 170 combine with the adjoining lateral strips 165 to define through channels 182 between the adjacent heating element loops 170. The two heating element loops 170 adjacent to the interior edges 158, 159 are connected to the adjacent interior edge 158 by a lateral bridge strip 155. The heating strips 169 of these heating element loops 170 combine with their adjacent interior edges 158 and the lateral bridge strips 155 to define through channels 183 between the heating element loops 170 and the interior edges 158, 159 of the supporting arms 151, 152.

In particular embodiments, the central heating portion 153 includes central support tabs 161 extending longitudinally from the ends of the heating strips 169. As shown in the illustrated embodiment, the central support tabs 161 may extend from the ends 166 of the heating element loops 170. Each central support tab 161 may be T-shaped with a stem 167 and a rectangular head 168. The central support tabs 161 may be sized and configured to engage surfaces or to be engaged by other structures in order to support and/or hold the central heating portion 153 of the heating element 150 in place within the structure of a micro-vaporizer. While the illustrated embodiment has two central support tabs 161 for each heating element loop 170, it will be understood that in other embodiments, some heating element loops 170 may have a central support tab 161 at just one end or may have no central support tabs 161 at all.

The two lateral bridge strips 155 serve to electrically connect the central heating portion 153 to the positive and negative support arms 151, 152. Aside from the bridge strips 155, the central heating portion 153 is otherwise isolated from the supporting arms 151, 152, thereby minimizing heat conduction from the central heating portion 153 to the supporting arms 151, 152. The array of heating strips 169 of the central heating portion 153 may be sized and configured to produce a heating profile for heating the spaces on both sides of the heating element 150 and vaporizable liquid within these spaces and/or passing through the channels 181, 182, 183. The array of heating strips 169 in combination with the support arms 151, 152 may also be sized to produce a particular flow area for passage of liquid and vaporization products through the heating element 150. The combination may be further configured to provide a desired overall heating element electrical resistance (i.e., the resistance between the positive and negative contact tabs 171, 172). Suitable combinations may provide an overall heating element resistance in a range of 0.0010 ohm to 5.2000 ohms. In certain embodiments, suitable combinations have been structured to provide an overall resistance in a range of 0.0015 ohm to 3.00000 ohms, and in more particular embodiments, in a range of 0.3500 ohm to 0.8000 ohm. It will be understood that the specific configuration of the central heating portion 254 and/or thickness of the heating element 250 may be tailored (in some cases, along with the power source) to the vaporizable liquid. For example, some liquids such as those containing cannabidiol (CBD), may need to be vaporized at a lower power to prevent scorching or burning. In particular embodiments, the central heating portion 254 may be configured to provide a resistance heating temperature in a range of 100-600° F. at a voltage of 1.0-4.2 V.

Returning now to FIGS. 3 and 4, the heating element 150 is disposed so that a portion of each support arm is embedded in the case structure 110. As will be discussed, this may be accomplished by molding some or all of the case structure around the heating element 150. In particular embodiments, the heating element 150 may be partially embedded within the case structure 110 at or near the outer surface of the lower case wall 112 with the central heating portion 153 in registration with the vaporization product flow window 118. In this way, the heating element's upper surface 152 faces inward toward the interior space 120 and the central heating portion of the heating element's lower surface 154 faces outward through the vaporization product flow window 118. In some embodiments, the positive and negative contact tabs 171, 172 may extend outside of the case structure 110. In particular embodiments, as in the heating element assembly 100, the contact tabs 171, 172 may be bent at a 90 degree angle from the main plane of the heating element 150 and positioned so that one surface is of each tab engages or is embedded within the right side case wall 114. This leaves the opposite surface of each tab exposed so that it can be contacted for establishing electrical communication.

Figure 5:
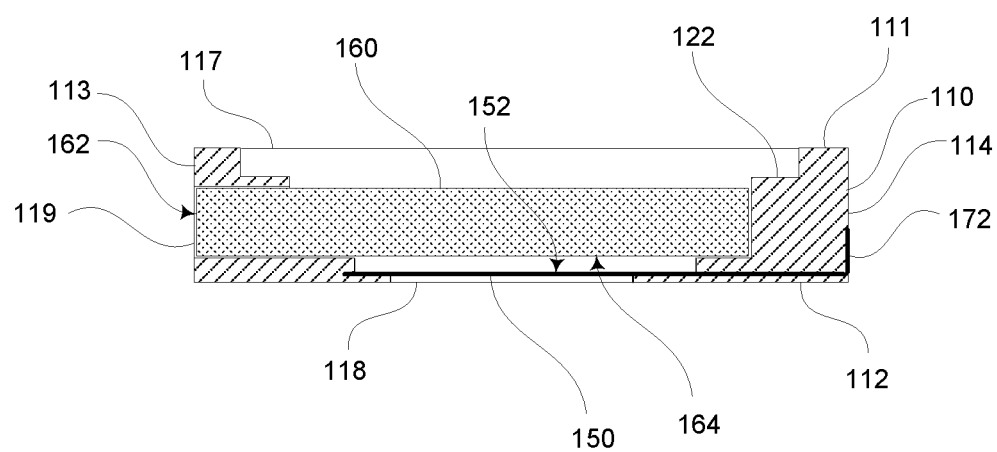
FIG. 5 is a front section view of the case structure, thin plate heating element, and liquid transport structure of the heating element assembly of FIG. 2.

As shown in FIGS. 5 and 6, the upper surface 152 of the thin plate heating element 150 is in close proximity to the outflow surface 164 of the liquid transport structure 160. When the heating element 150 is energized, vaporizable liquid within the liquid transport structure 160 adjacent the outflow surface 164 is heated to vaporization. When a pressure drop is applied outside the vaporization product flow window 118, vaporized and unvaporized liquid are drawn from the outflow surface 164 and through the flow channels 181, 182, 183 of the heating element 150. This serves to further heat the vaporization products to vaporize the unvaporized liquid. As will be discussed, these products may be further heated within a vaporization chamber of vaporizer device external to the heating element assembly 100. The pressure drop may also serve to draw additional vaporizable liquid from the reservoir into and through the liquid transport structure 160.

With reference to FIGS. 10-16 a heating element assembly 200 according to another illustrative embodiment of the invention has a generally rectangular prism-shaped case structure 210 with a thin wall heating element 250 partially embedded in a portion of the case structure 210. The case structure 210 has an interior space 220 in which may be disposed a liquid transport structure 260.

The case structure 210 has upper and lower case walls 211, 212, a left (or reservoir) side case wall 213, a right (or contact) side case wall 214, and front and back case walls 215, 216 that collectively define the case interior space 220. The lower wall 212 has a vaporization product flow window 218 formed there-through. The thin wall heating element 250 is partially embedded in the lower wall 212 in such a way that it spans flow window 218. As before, the upper case wall 211 has an access opening 217 formed there-through. The access opening 217 is sized and configured to allow access to the case interior 220 during the construction of the assembly 200. A top wall closure member 230 may be received into the access opening 217 to rest on a closure support ledge 222 in the interior 220, thereby closing off the opening 217.

The reservoir side case wall 213 has a reservoir communication window 219 formed there-through. The reservoir communication window 219 is sized and configured to provide fluid communication between a vaporizer device reservoir (or a flow structure leading from such a reservoir) and the case interior 220 when the heating element assembly 200 is installed in the vaporizer device. A liquid transport structure 260 is positioned within the case interior 220 at or adjacent the window 219. In this way, the liquid transport structure 260 may be placed in communication with liquid in the vaporizer reservoir by positioning the assembly 200 within a vaporizer so that the reservoir communication window 219 is in registration with a passage into the vaporizer's reservoir. The liquid transport structure 260 is configured for drawing vaporizable liquid from a reservoir through the upstream intake surface 262 into the structure 260 and transporting the liquid to the downstream outflow surface 264 where the liquid may be heated to vaporization by the heating element 250. As before, it will be understood that the liquid transport structure 260 may have any of a variety of shapes and the interior space 220 may be shaped correspondingly to receive and retain the transport structure 260.

The thin plate heating element 250 may be configured for placement in contact with or adjacent the downstream outflow surface 264 of the liquid transport structure 260. While similar to the heating element 150 of the previous embodiment, the heating element 250 includes stand-offs extending at an angle (or angles) from its main body. As before, the thin plate heating element 250 has a peripheral conduction portion made up of a positive support arm 251 and a negative support arm 252 and a central heating portion 253 positioned between the support arms 251, 252. The support arms 251, 252 have interior edges 258 facing inward toward one another and toward the central heating portion 253 and exterior lateral edges 259 facing outward. The interior edges 258 are parallel to one another and to a longitudinal axis 254. The positive support arm 251 includes a positive contact tab (or positive contact) 271 and the negative support arm 252 includes a negative contact tab (or negative contact) 272 extending in a longitudinal direction away from the central heating portion 253. In some embodiments (e.g., the illustrated embodiment), at least a portion of the contact tabs 271, 272 angle away from the plane defined by the support arms 251, 252. In particular embodiments, the contact tabs 271, 272 include a portion at right angles to the plane of the support arms 251, 252. The positive and negative contact tabs 271, 272 are configured for making electrical contact with corresponding elements of an electrical power circuit in communication with a power source.

The heating element 250 has a plurality of peripheral support tabs 256 extending from each support arm exterior edge 259. At least a portion of each tab 256 extends upward from the exterior edge at an angle relative to the surface of the support arm adjacent the exterior edge 259. In particular embodiments where the central heating portion 253 and the support arms 251, 252 are coplanar, the peripheral support tabs 256 each extend at a right angle from the plane of the central heating portion 253 and the support arms 251, 252. In some embodiments (including the illustrated embodiment), all of the peripheral support tabs 256 extend in the same direction, while in others, some tabs 256 may extend in one direction and other tabs may extend in the opposite direction. While in typical embodiments, all of the tabs 256 extending in the same direction will have the same length $L_{pt}$, in some embodiments the tabs 256 may have varying lengths to accommodate variable structures within the vaporizer.

The central heating portion 253 is made up of an array of spaced apart but interconnected heating strips 269. These heating strips 269 are parallel to one another and to the longitudinal axis 254. In particular embodiments, the heating strips 269 are divided in to pairs, with the strips 269 of each pair being connected to one another at both ends to form a heating element loop 260 surrounding a through channel 281 through the material. Adjacent heating element loops 260 (e.g., loop 260a and loop 260b) are connected to one another by a lateral strip 265. Adjacent strips 269 of adjacent loops 260 combine with the adjoining lateral strips 265 to define through channels 282 between the adjacent loops 260. The two heating loops 260 adjacent to the interior edges 258, 259 are connected to the adjacent interior edge 258 by a lateral bridge strip 255. The side strips 269 of these loops combine with their adjacent interior edges 258 and the lateral bridge strips 255 to define through channels 283 between the loops 260 and the supporting arm edges 258, 259.

The central heating portion 253 includes central support tabs 261 extending longitudinally from the ends of the heating element loops 260. Each central support tab 261 may have a stem 267 and a tab head 268. At least a portion of each tab head 261 extends upward or downward from the heating element loop 260 at an angle relative to the surface of the loop 260. In particular embodiments where the central heating portion 253 and the support arms 251, 252 are coplanar, the central support tabs 261 each extend at a right angle from the plane of the central heating portion 253 and the support arms 251, 252. In some embodiments (including the illustrated embodiment), all of the peripheral support tabs 261 extend in the same direction, while in others, some tabs 261 may extend in one direction and other tabs 261 may extend in the opposite direction. While in typical embodiments, all of the tabs 261 extending in the same direction will have the same extension length (i.e., the length of the portion of the tab head 268 extending away from the main plane) $L_{ct}$, in some embodiments the tab head extension portions may have varying lengths to accommodate variable structures within the vaporizer.

The peripheral support tabs 256 and the central support tabs 261 may be sized and configured to engage surfaces or to be engaged by other structures in order to support and/or hold the central heating portion 253 of the heating element 250 in place within the structure of a micro-vaporizer. In some embodiments, the peripheral support tabs 256 may all extend in one direction away from the main plane of the heating element 250 while the central support tabs 261 extend in the opposite direction away from the main plane of the heating element 250. When all of the peripheral and central support tabs 256, 261 extend in the same direction (as in the illustrated embodiment), their lengths $L_{pt}$ and $L_{ct}$ may be the same in order to provide support relative to a constant planar surface parallel to the main plane of the heating element 250. In particular embodiments, the peripheral support tabs 256 may be configured so that at least a portion of the tabs 256 can be embedded within the case structure 110 to provide support for the heating element 250 within the assembly 200.

In the heating element assembly 200, the thin plate heating element 250 is disposed so that a portion of each support arm is embedded in the case structure 210. In some embodiments, a portion of one or more of the peripheral support tabs 256 may also be embedded within the case structure 210. In particular embodiments, the heating element 250 may be partially embedded within the case structure 210 at or near the outer surface of the lower case wall 212 with the central heating portion 253 in registration with the vaporization chamber window 218. In this way, the heating element's upper surface 252 faces inward toward the case interior 220 and the central heating portion of the heating element's lower surface 254 faces outward through the vaporization chamber window 218. In some embodiments, the positive and negative contact tabs 271, 272 may extend outside of the case structure 210. In particular embodiments, as in the assembly 200, the contact tabs 271, 272 may be bent at a 90 degree angle from the main plane of the heating element 250 and positioned so that one surface is of each tab engages or is embedded within the right side case wall 214. This leaves the opposite surface of each tab exposed so that it can be contacted for establishing electrical communication.

Figure 15:
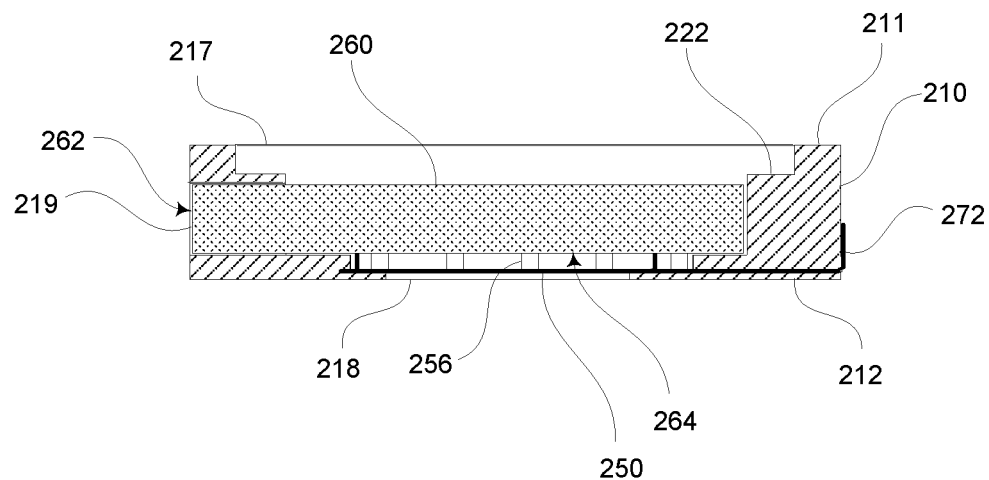
FIG. 15 is a front section view of the case structure and thin plate heating element of FIG. 13 with the addition of a fluid transport structure.
Figure 16:
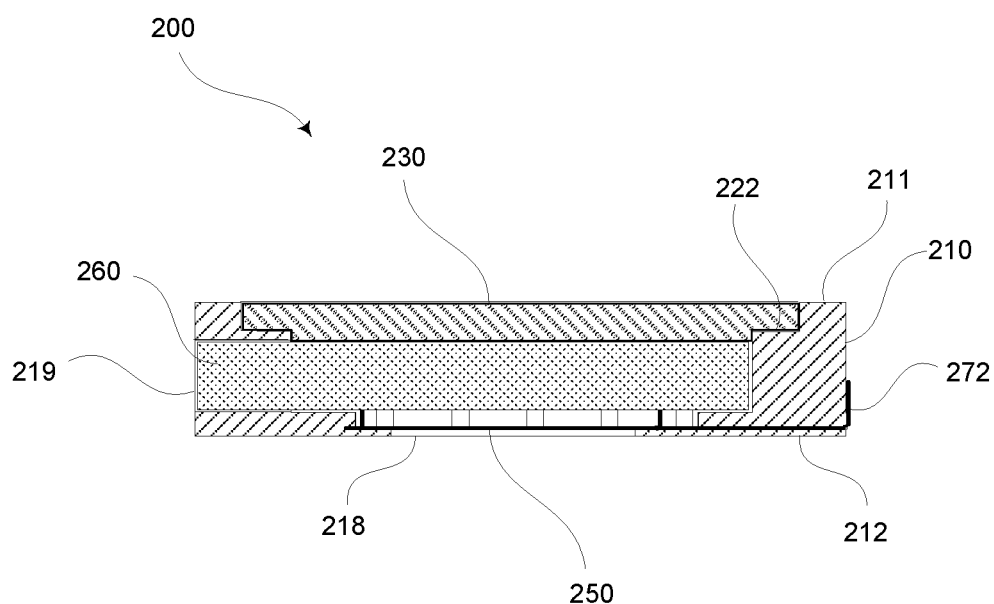
FIG. 16 is a front section view of a heating element assembly according to an embodiment of the invention incorporating the case structure, thin plate heating element, and fluid transport structure of FIG. 15.

As shown in FIGS. 15 and 16, the upper surface 252 of the thin plate heating element 250 is in close proximity to the outflow surface 264 of the liquid transport structure 260. The spacing between the upper heating element surface 252 and the transport structure outflow surface 264 is maintained and the transport structure 260 is supported by the peripheral support tabs 256 and the central support tabs 261. When the heating element 250 is energized, vaporizable liquid within the liquid transport structure 260 adjacent the outflow surface 264 is heated to vaporization. When a pressure drop is applied outside the vaporization window 218, vaporized and unvaporized liquid are drawn from the outflow surface 264 and through the flow channels 281, 282, 283 of the heating element 250. This serves to further heat the vaporization products to vaporize the unvaporized liquid.

Figure 17:
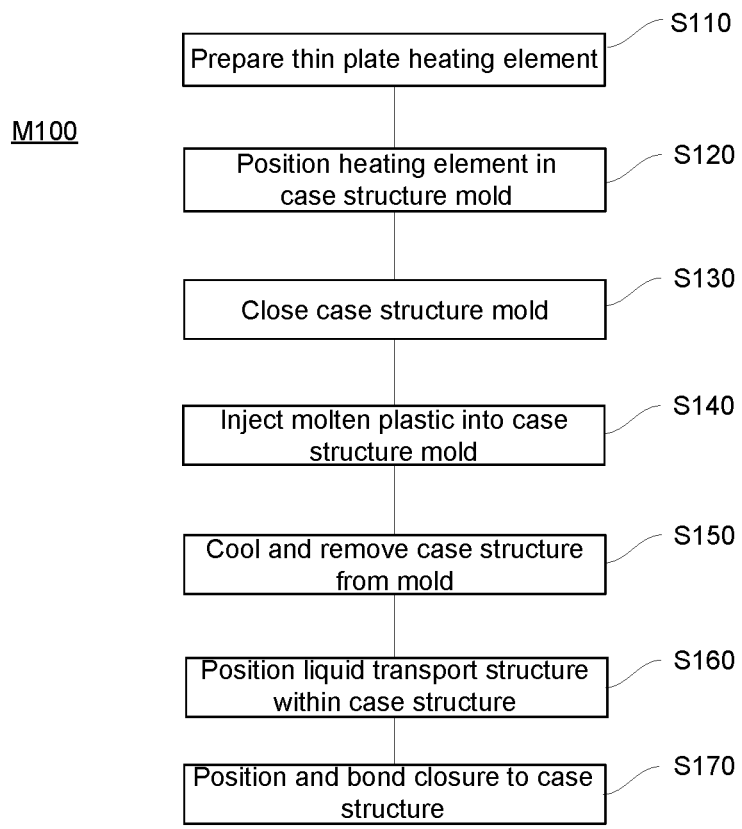
FIG. 17 is a flow diagram of the actions in a method of manufacturing a heating element assembly according to an embodiment of the invention.

FIG. 17 illustrates a method M100 of manufacturing a vaporizer heating element assembly according to an embodiment of the invention. At S110 of the method M100, a thin plate heating element is prepared. This may include, for example, providing a thin sheet of conductive material and cutting a heating element blank from the sheet according to a desirable pattern. The pattern may established according to desirable electrical resistance, heating, and flow-through characteristics for the heating element. In particular embodiments, the pattern may be established to produce a heating element similar to any of those described above. Preparation of the thin plate heating element may further include bending contact tabs and support tabs to a desired angle. At S120, the thin plate heating element is positioned within an injection mold configured for receiving molten plastic material and forming it into the desired case structure for the heating element assembly. The injection mold is further configured to support the thin plate heating element during the injection process so that a desired portion of the heating element is embedded within the resulting plastic case structure. At S140, molten plastic is injected into the case structure mold. It will be understood that the case structure may be molded in stages or may be produced through a sequence of molding operations. At S150, the molded case structure is cooled and removed from the mold. In some embodiments, extraneous material may be removed from the molded structure. The resulting case structure includes a reservoir window, a vaporization chamber window and an access opening as previously described. The case structure also has the thin plate heating element partially embedded therein and placed at or adjacent the vaporization chamber window. At S160, a liquid transport structure is inserted into the interior of the case structure through the access opening and positioned so that its downstream outflow surface is adjacent the heating element. In some embodiments, the liquid transport structure is supported only by internal case structure. In other embodiments, the liquid transport structure is supported, at least in part, by support tabs extending from the heating element. At S170 a closure is positioned within the access opening and bonded to the case structure so as to seal the access opening and to hold the liquid transport structure in place within the case interior. The closure may be bonded in any suitable manner. In particular embodiments, the closure is ultrasonically welded to the case structure. In such embodiments, the final case structure, including the closure, may be formed exclusively from a single plastic material so that the final heating element assembly consists only of a single material case structure, the thin plate heating element and the liquid transport structure.

Figure 18:
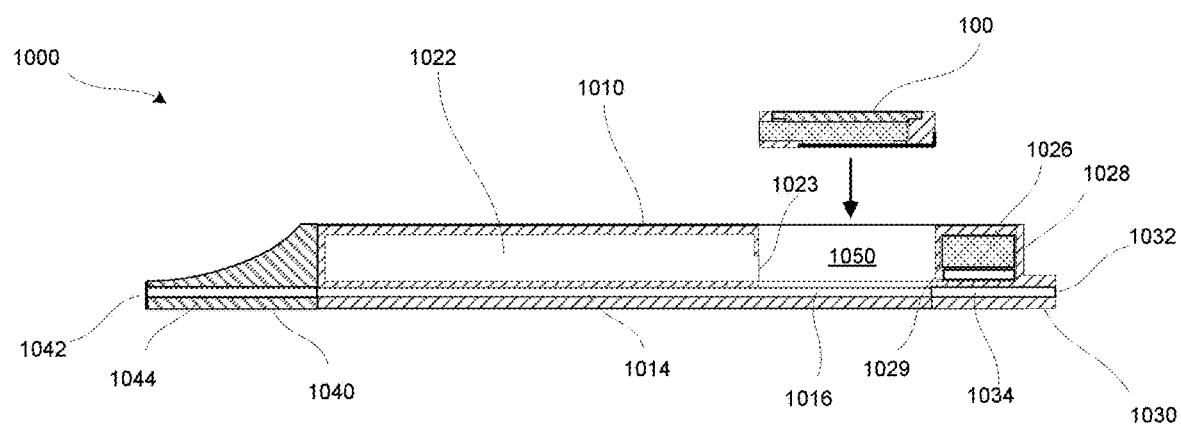
FIG. 18 is a front section view of a partially assembled vaporizer according to an embodiment of the invention.
Figure 19:
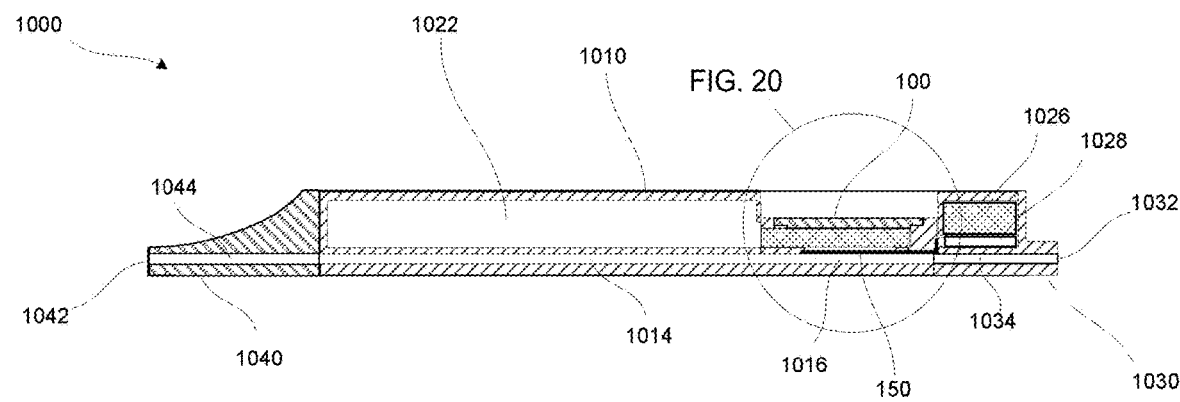
FIG. 19 is a front section view of the vaporizer of FIG. 18 with the heating element assembly installed.
Figure 20:
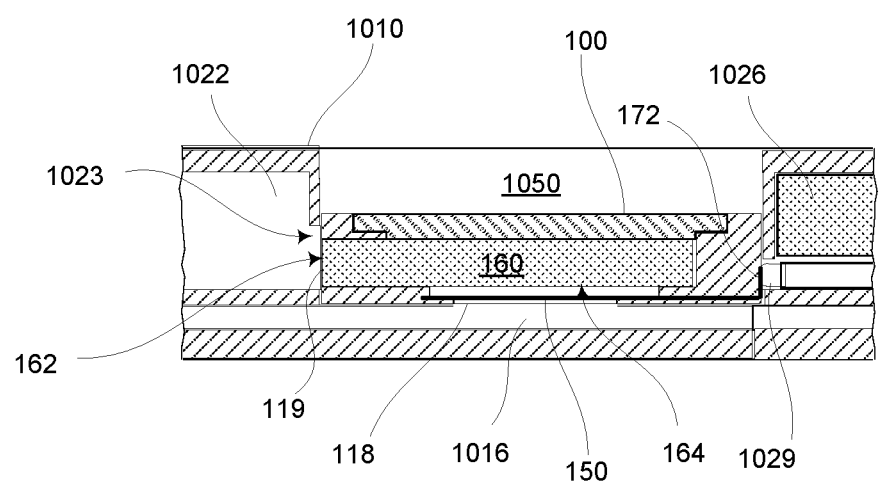
FIG. 20 is an enlarged view of a portion of the vaporizer of FIG. 19.

The heating element assemblies of the invention are structured so that they can be used in a variety of modular vaporizer configurations. These modular vaporizers would have the usual liquid reservoir, power supply, activation system, and air flow passages and would be configured to separately receive a heating element assembly and a vaporizable liquid to make the vaporizer operational. An illustrative example of such a modular vaporizer is shown in FIGS. 18-20. The illustrated vaporizer 1000 has a case or main body 1010 to which is attached an air intake section 1030 and a mouthpiece section 1040. The main body 1010 may be a single integral structure or may be made up of multiple sub-structures. The air inlet section 1030 has an air intake (or inlet) passage 1034 in communication with an air inlet (or air inlet port) 1032 through which air may be drawn from the atmosphere surrounding the vaporizer 1000. The mouthpiece section 1040 has a vaporization products exit passage (or vaporization products passage) 1044 in communication with an exit port (or vaporization products outlet) 1042 through which vaporization products may be drawn (e.g., by inhalation by a user). Within the main body 1010 of microvaporizer 1000 is disposed a main passageway 1014 in communication with the intake passage 1034 and the exit passage 1044. A portion of the main passageway 1014 may be configured to provide a vaporization section 1016.

Also disposed within the main body 1010 is a reservoir 1022 configured for receiving a vaporizable liquid. The liquid reservoir 1022 may be configured as a simple tank in which the liquid is disposed. In some embodiments, the reservoir 1022 may comprise an adsorptive or absorptive material or structure that retains the vaporizable liquid. In either case, the reservoir 1022 has an exit port 1023 through which vaporizable liquid can be withdrawn from the reservoir 1022. The vaporizer 1000 also includes electrical circuitry that includes a power source (e.g., a battery) 1026 in electrical communication with a control processor 1028. The vaporizer 1000 may also include an activation mechanism (not shown) that allows a user to selectively activate the device, thereby causing power to flow from the power source 1026.

The interior of the main body 1010 is formed with a receiving well 1050 sized and configured to receive a heating element assembly such as the heating element assembly 100 of FIGS. 2-6. The main body 1010, the reservoir 1022 and the electrical circuitry are arranged so that insertion of the heating element assembly 100 into the installed configuration shown in FIGS. 19 and 20 results in (1) the reservoir window 119 of the heating element assembly 100 being in registration with the reservoir exit port 1023 and (2) the contact tabs 171, 172 engaging complementary contacts 1029 of the electrical circuitry. This configuration allows for fluid communication between the liquid transport structure 160 and the interior of the reservoir 1022 and establishes selective electrical communication between the power source 1026 and the heating element 150. The heating element assembly 100 may be retained in this position by any of various means (not shown), including mechanical fasteners or detents, bonding or addition of a closure element to seal off the well 1050.

With the heating element assembly 100 in its installed configuration, it can be seen that the heating element 150 is positioned so that it is parallel to the direction of air flow into and through the vaporization section 1016 and so that it, in effect, provides a part of the boundary surrounding the vaporization section 1016. When a vaporizable liquid is added to the reservoir, the vaporizer 1000 is ready for use. Upon activation, the heating element 150 begins to heat the outflow surface 164 of the liquid transport structure 160. Vaporizable liquid, typically comprising one or more active materials, drawn from the reservoir 1022 to the outflow surface 164 is heated to vaporization. As this occurs, the user inhales through the mouthpiece passage 1042, drawing air into the intake passage 1034 and the main passage 1014. At the same time, vapor products and/or unvaporized liquid are drawn through the heating element 150 into the vaporization section 1016 where they are further heated and mixed with air in the main passage 1014. The resulting mixture of air and vaporization products is then drawn through the passageway 1014 into and through the mouthpiece passage 1044 and out through the exit port 1042.

As used herein, the term "active material" refers to any material that controllably alters or adds to the vaporization products of the device. Depending on the application, active materials can include, without limitation, plant material, minerals, deodorizing agents, fragrances, insect repellants, medications, and disinfectants and any material or structure containing or incorporating any of the foregoing.

In the specific instance of personal vaporizers, active materials may include flavorant substances that augment the flavorant of the vaporizable liquid. These may include, without limitation, marijuana, hemp, cannabidiol (cbd), citronella, geraniol, mint, thyme, tobacco, *Salvia dorrii*, *Salvia*, *Passiflora incarnata*, *Arctostaphylos uva-ursi*, *Lobelia inflata*, lemon grass, cedar wood, clove, cinnamon, coumarin, helio, vanilla, menthol, eucalyptus, peppermint, rosemary, lavender, licorice, and cocoa and any material or structure containing or incorporating any of the foregoing.

It will be understood that there may be many other configurations for the vaporizer components and air passageways. In some configurations, there may be multiple air inlet ports and the air flow path from the air inlet ports to the vaporization chamber may comprise one or more intermediate passageways and/or chambers. There may also be additional liquid flow passages and/or wicking structures to provide communication between the reservoir 1022 and the liquid transport structure 160.

While the foregoing illustrates and describes exemplary embodiments of this invention, it is to be understood that the invention is not limited to the construction disclosed herein. The invention can be embodied in other specific forms without departing from the spirit or essential attributes.

What is claimed is:

1. A vaporizer heating element assembly comprising:
   a case structure having a plurality of walls collectively defining a case interior, the plurality of walls including an upper wall having an access opening formed therethrough, a left wall having a reservoir window formed there-through, and a lower wall having a vaporization window formed there-through;
   a thin plate heating element formed from an electrically conductive material, the thin plate heating element being positioned in the case structure parallel to the lower wall and adjacent the vaporization window;
   a liquid transport structure having a liquid intake surface and a liquid outflow surface, the liquid transport structure being configured for transporting a vaporizable liquid by capillary action from the liquid intake surface to the liquid outflow surface and being disposed within the case interior so that the liquid intake surface is adjacent the reservoir window and the liquid outflow surface is adjacent or in contact with a surface of the thin plate heating element; and
   an access closure disposed within the access opening and attached to the upper wall, the access closure being sized and configured to seal the access opening.

2. The vaporizer heating element assembly according to claim 1 wherein the thin plate heating element comprises positive and negative contact tabs extending through one of the plurality of walls so that a surface portion of each contact tab is exposed outside the case structure.

3. The vaporizer heating element assembly according to claim 1 wherein at least a portion of the thin plate heating element is embedded within one or more of the plurality of walls.

4. The vaporizer heating element assembly according to claim 1 wherein the thin plate heating element comprises:
   a peripheral conduction portion in contact with the case structure, and
   a central heating portion in electrical communication with the peripheral conduction portion, the central heating portion being in registration with the vaporization window and being spaced apart from the case structure.

5. The vaporizer heating element assembly according to claim 4 wherein the central heating portion comprises a plurality of spaced apart parallel heating strips, spaces between said heating strips defining flow channels through the thin plate heating element.

6. The vaporizer heating element assembly according to claim 4 wherein the central heating portion is configured to provide a resistance heating temperature in a range of 100-600° F. at a voltage in a range of 1.0-4.2 V.

7. The vaporizer heating element assembly according to claim 4 wherein the peripheral conduction portion comprises spaced apart positive and negative support arms, and wherein a first bridge strip connects the positive support arm to the central heating portion and a second bridge strip connects the negative support arm to the central heating portion.

8. The vaporizer heating element assembly according to claim 7 wherein the thin plate heating element further comprises:
a plurality of peripheral support tabs extending from an exterior edge of each of the positive and negative support arms, at least a portion of each support tab being in contact with the case structure.

9. The vaporizer heating element assembly according to claim 8 wherein at least a portion of each support tab is embedded within one of the plurality of walls.

10. The vaporizer heating element assembly according to claim 7 wherein the thin plate heating element further comprises:
a plurality of central support tabs extending at an angle from the central heating portion, the central support tabs being in contact with the liquid outflow surface of the liquid transport structure.

11. The vaporizer heating element assembly according to claim 7 wherein the thin plate heating element further comprises:
a positive contact tab extending from an end of the positive support arm; and
a negative contact tab extending from an end of the negative support arm,
wherein the positive and negative contact tabs extend through one of the plurality of walls so that a surface portion of each contact tab is exposed outside the case structure.

12. The vaporizer heating element assembly according to claim 1 wherein the liquid transport structure is or includes a wick structure.

13. The vaporizer heating element assembly according to claim 11 wherein the liquid transport structure is or includes a composite wick structure comprising a wicking material and an active material selected to impart a desired characteristic to the vaporizable liquid.

14. The vaporizer heating element assembly according to claim 12 wherein the wick structure comprises a plurality of organic or inorganic fibers.

15. The vaporizer heating element assembly according to claim 1 wherein the plurality of walls are formed as a single integral structure.

16. The vaporizer heating element assembly according to claim 15 wherein the single integral structure is formed from an injected molded thermoplastic material.

17. A method of manufacturing a vaporizer heating element assembly, the method comprising:
providing a thin plate heating element formed from an electrically conductive material;
positioning the thin plate heating element within an injection mold;
injecting molten plastic into the injection mold to produce a molded plastic case structure in which the thin plate heating element is positioned, the molded plastic case structure having a plurality of walls collectively defining a case interior, the plurality of walls including an upper wall having an access opening formed there-through, a left wall having a reservoir window formed there-through, and a lower wall having a vaporization window formed there-through, the thin plate heating element being positioned parallel to the lower wall adjacent the vaporization window with a portion of the thin plate heating element being embedded within one or more of the plurality of walls;
removing the molded plastic case structure and the thin plate heating element from the injection mold;
providing a liquid transport structure having a liquid intake surface and a liquid outflow surface and being configured for transporting liquid by capillary action from the liquid intake surface to the liquid outflow surface;
inserting the liquid transport structure into the case interior through the access opening and positioning the liquid transport structure so that the liquid intake surface is adjacent the reservoir window and the liquid outflow surface is adjacent or in contact with a surface of the thin plate heating element; and
sealing the access opening with a closure element sized and configured to be partially received into the access opening.

18. The method according to claim 17 wherein the action of sealing the access opening includes ultrasonically bonding the closure element to the upper wall of the case structure.

19. The method according to claim 17,
wherein the thin plate heating element comprises a peripheral conduction portion, and a central heating portion in electrical communication with the peripheral conduction portion, and
wherein in the molded plastic case structure, the peripheral conduction portion is in contact with one or more of the plurality of walls, and the central heating portion is in registration with the vaporization window and spaced apart from the case structure.

20. A vaporizer comprising:
a vaporizer housing having a housing interior and an exterior;
a reservoir disposed within the housing interior, the reservoir having a reservoir exit port and being configured for selectively retaining a vaporizable liquid therein;
an air inlet passage in fluid communication with the exterior via an inlet port;
a vaporization chamber within the housing interior in fluid communication with the air inlet passage;
a vaporization products passage in fluid communication with the vaporization chamber and with the exterior via a vaporization products outlet;
electrical circuitry comprising a power source, a control processor, and positive and negative heating element contacts, the control processor being configured for controlling application of power from the power source to the heating element contacts;
a heating element receiving well formed within the housing interior; and
a heating element assembly operably disposed within the receiving well, the heating element assembly comprising:
a case structure defining a case interior and having a reservoir window and a vaporization window formed there-through, the case structure and receiving well being collectively configured so that the reservoir window is in registration with the reservoir exit port and the vaporization window is adjacent the vaporization chamber, a thin plate heating element formed from an electrically conductive material, the thin plate heating element being positioned within the case interior so that at least a portion of the heating element is adjacent the vaporization window, and a liquid transport structure having a liquid intake surface and a liquid outflow surface, the liquid transport structure being disposed within the case interior so that the liquid intake surface is adjacent the reservoir window and the liquid outflow surface is adjacent or in contact with a surface of the thin plate heating element.

21. The vaporizer according to claim 20 wherein the thin plate heating element further comprises positive and negative contact tabs extending through a wall of the case structure so that the positive contact tab is in contact with the positive heating element contact and the negative contact tab is in contact with the negative heating element contact.

\* \* \* \* \*